United States Patent

Ward

[11] Patent Number: 5,099,832
[45] Date of Patent: Mar. 31, 1992

[54] PACKAGED STERILE ADHESIVE DRESSING

[75] Inventor: William J. Ward, Hull, United Kingdom

[73] Assignee: Smith & Nephew plc, England

[21] Appl. No.: 404,082

[22] Filed: Sep. 7, 1989

Related U.S. Application Data

[63] Continuation-in-part of Ser. No. 345,987, May 2, 1989, Pat. No. 5,000,172.

[30] Foreign Application Priority Data

Sep. 7, 1988 [GB] United Kingdom ............... 8820944
Dec. 14, 1988 [GB] United Kingdom ............... 8829151

[51] Int. Cl.⁵ .................. A61F 13/00; A61F 18/00; A61L 15/00; A61B 17/06
[52] U.S. Cl. .................................. 602/57; 206/441; 602/41
[58] Field of Search ............... 128/155, 156, 888; 206/440, 441

[56] References Cited

U.S. PATENT DOCUMENTS

| | | | |
|---|---|---|---|
| 2,897,961 | 8/1959 | Bush | 206/441 |
| 2,973,859 | 3/1961 | Schladermundt et al. | 206/441 |
| 3,072,249 | 1/1963 | Tritsch | 206/441 |
| 4,598,004 | 7/1986 | Heinecke | 428/40 |
| 4,706,662 | 11/1987 | Thompson | 128/155 |

Primary Examiner—Randall L. Green
Assistant Examiner—Paul Prebilic
Attorney, Agent, or Firm—Rosenman & Colin

[57] ABSTRACT

An adhesive dressing comprises a backing layer having a pressure sensitive adhesive layer over one surface thereof, a removable protector comprising two parts which covers the adhesive layer and extends beyond the backing layer at one or more edges and a conformable, support layer which is reversibly attached to the non-adhesive surface of the backing layer and extends beyond the backing layer at one or more of said edges. The product comprises two parts, the first being V-shaped and having portion extending away from the adhesive surface while the second part, also has a portion extending away from the adhesive surface and which overlies the V-shaped part.

20 Claims, 1 Drawing Sheet

PACKAGED STERILE ADHESIVE DRESSING

This is a continuation-in-part of my copending application Ser. No. 07/345,987 filed May 2, 1989, now U.S. Pat. No. 5,000,172 which is incorporated herein by reference.

The present invention relates to an adhesive dressing which comprises a backing layer which has on one surface a pressure sensitive adhesive layer covered by a removable release liner and attached to the other surface a support layer. The adhesive dressing may be used to treat wounds such as burns, abrasions, ulcers and surgical incisions and as a protective dressing to cover for example an indwelling catheter site.

One type of adhesive dressing which has been used for many years comprises a thin, film, moisture vapour permeable polymeric material coated on one surface with an adhesive. The dressing was presented for use with a protector layer over the adhesive and adhesive-free handles at a pair of opposed edges. Subsequently alternative modes of presentation were introduced to ease application of the thin film product for the inexperienced particularly in an effort to prevent the dressing creasing and adhering to itself during application. If this occurs then the dressing must be discarded. One such -mode of presentation required the presence of a carrier means usually of a material stiffer than the adhesive coated film adhered to the non-adhesive surface of that film. To apply such dressings the release liner was removed, the adhesive coated film was adhered to the patient and then the carrier removed Dressings of this type are described in for example United Kingdom Patent Application No. 2120104, European Patent Nos. 51935, 66899 and 81990 and U.S. Pat. Nos. 4,372,303, 4,374,520, 4,513,739, 454371 and 4,600,001.

A simple way of presenting thin film dressings for application to a patient has been found which avoids the complexity of previously known dressings, which avoids the requirement of tearing or cutting any part of the dressing during application except when fitting to an awkward body part such as the heel but even then as with the normal dressing the presence of the support layer reduces the risk of the dressing adhering to itself or being contaminated by accidental contact with non-sterile surfaces If the dressing has to be cut as when fitting an awkward body part such as the heel, then the presence of the support layer over the whole of the remainder of the dressing facilitates its application. This is in contrast to, for example, those dressings which use devices such as handles or frames to support as this support may be lost if these devices are cut through.

An adhesive dressing which comprises a backing layer having a pressure sensitive adhesive layer over one surface thereof, a removable protector which covers the adhesive layer and extends beyond the backing layer at one or more edges and a conformable support layer which is reversibly attached to the non-adhesive surface of the backing layer and extends beyond the backing layer at one or more of said edges. Wherein said protector comprises first and second parts, the first part having a portion extending away from the adhesive surface and bent back to form a V-shape and the second part having a portion extending away from the adhesive surface and overlying the V-shaped first part.

The support layer is conformable by which it is meant that the support layer will conform to the contours of a surface to which it is applied. Aptly the support layer may be left attached to the backing layer without detracting seriously from the performance of the dressing, though it is preferred to remove the support layer.

Suitably the removable protector and the support layer extend beyond the backing layer at one edge but more suitably the removable protector and support layer extend beyond the backing layer at two opposed edges.

The term 'opposed edges' also includes opposed edge regions, in these instances, such as with circular or oval dressings where the limits of each separate edge may not be readily apparent and the edges may merge.

The protector and support layers may extend peripherally beyond the backing layer.

Suitably the backing layer may comprise any of those materials which are conventionally employed to form thin film surgical dressing Suitable materials include those described in United Kingdom Patent No. 1280631, European Patents Nos. 51935, 91800 and 178740. Particularly apt materials are polyurethanes, for example polyester or polyether polyurethanes known as Estanes (Trade Mark). Other apt materials are elastomeric polyether polyesters, for example those known as Hytrels (Trade Mark) and polyether polyamides, for example those known as Pebaxes (Trade Mark). Other favoured materials include hydrophilic polymers such as hydrophilic polyurethanes including those described in United Kingdom Patent No. 2093190B, especially the polyurethane described in Example 2 therein. Such materials will typically take up from 5 to 95% by weight of water.

The materials employed in the dressings of the invention may be moisture vapour permeable.

The moisture vapour transmission rate of the materials employed in the present invention may be measured by a procedure known as the Payne Cup method. The method uses a cup 1.5 cm deep with a flanged top. The inner diameter of the flange is such to provide an area for moisture vapour transmission of 10 cm$^2$. In this method 10 ml of distilled water is added to the cup and a sample of the material under test, large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed as in g/m$^2$/24 hrs at 37° C. at 100% to 10% relative humidity difference. Hereinafter the units for moisture vapour transmission will be abbreviated to g m$^{-2}$.

Suitably the backing layer is moisture vapour permeable and has a moisture vapour transmission rate of at least 500 g m$^{-2}$, more suitably at least 1200 g m$^{-2}$ and preferably at least 1600 g m$^{-2}$.

Suitably the backing layer has thickness of from 15 to 100 $\mu$m, more suitably 20 to 80 $\mu$mm and preferably 25 to 50 $\mu$m, for example 27.5$\mu$, 30 $\mu$m, 35 $\mu$m and 40 $\mu$m.

Aptly the pressure sensitive adhesive layer may be formed from an adhesive which is conventionally used for contact with the skin. Suitable adhesives include polyvinyl alkyl ether adhesive and acrylate ester copolymer adhesives. Suitable adhesives are described in United Kingdom Patent No. 1280631 and European Patents Nos. 35399 and 51935. Preferably the adhesive is a polyvinyl ether adhesive or an acrylate ester copolymer adhesive formed by the copolymerisation of 2-ethylhexyl acrylate, butyl acrylate and acrylic acid.

Suitably the adhesive layer is from 15 to 65 μm thick, for example 20 to 40 μm thick and is applied at a weight per unit area of 10 to 75 gsm, more suitably 15 to 65 gsm and preferably 25 to 40 gsm.

Suitably the removable protector is a silicone coated release paper. Suitably the removable protector may have a weight per unit area of 100 to 140 gsm, and preferably 110 to 130 gsm, for example 120 gsm. The removable protector may be divided into two or more pieces. Preferable at least one of the protector pieces is significantly larger than the other or others and covers a major proportion of the adhesive layer. It is desirable that the stripping load of the support layer from the backing layer is greater than that of the protector from the adhesive layer otherwise there is a risk that the support layer would peel from the backing layer before the protector can be removed.

The removable protector may extend less beyond the edge of the backing layer than the corresponding support layer. This facilitates grasping the support layer in one hand and the protector in the other.

The smaller piece has a portion extending away form the adhesive surface and is folded back to form a V-shape with the fold line or apex of the V being away from the edge of the dressing is towards the interior of the dressing. The larger piece of the removable protector then covers the remaining adhesive surface and overlaps onto the V-shaped piece.

Preferably at least one, more preferably, both edges of the V-shaped part extends beyond the edge of the backing layer. The edge of the overlying portion of the second part also extends beyond the edge of the backing layer.

In use the support layer and the V-shaped piece are gripped in one hand and the second part of the adhesive protector peeled off with the other. Alternatively only the V-shaped piece may be gripped. When the major portion of the dressing is in place the V-shaped piece may then be removed and the remainder of the dressing applied to the patient. Then if desired the support layer is removed. Alternatively, if desired, the conformability of the dressing may be increased by removing the V-shaped piece first and the dressing handled aseptically by the projecting edges of the support layer.

Suitably the support layer is formed from a polymeric film or a paper. The support layer may be attached to the backing layer by virtue of casting or extruding the backing layer onto the support layer thereby forming an attachment which is easily reversed. Suitably the support layer maybe formed from, for example, a transparent polymeric film such as a polethylene or polypropylene film or from an opaque silicone or polyethylene coated paper.

The support layer may carry markings including those in the form of a grid or concentric circles and the like whereby the progress of a healing wound or ulcer may be monitored. In this case the support layer remains on the backing layer.

The dressings of the present invention possess advantages over those of the prior art in that the dressing can be readily handled with one hand, the major portion of the adhesive service of the dressing can be readily presented without creasing the dressing and yet the dressing is securely and aseptically held and, once applied, the remaining supporting and protecting components of the dressing can be easily removed without disturbing the portion of the dressing applied.

Suitably the adhesive dressing has a backing layer and adhesive layer which are translucent and preferably are transparent.

In a preferred embodiment of the invention, the support layer, backing and adhesive layer, constituting the dressing to be applied, are each sufficiently transparent such that the wound or catheter site can be viewed through the dressing once one or more of the adhesive protectors have been removed. The provision of transparent support layers together with other transparent dressing components not only enables the dressing to be both readily handled during application, usually with use of only one hand, but also enables the location of the dressing to be visible and for the dressing to be accurately positioned at the desired location.

The adhesive dressing may be prepared by casting a solution of the polymer which is to form the backing layer onto a long strip of the film which is to form the support layer. An adhesive may be cast or transfer coated onto the backing layer. The backing layer and adhesive layer may then be trimmed to the correct width on the support layer. The removable protector may then be applied to the adhesive surface in one or two pieces as described hereinbefore. The material so formed may be further trimmed and then cut transversely to form dressings of the appropriate size. The dressings may have an area equivalent to 5×5 cm to 20×20 cm, for example 5×7.5 cm, 7.5×10 cm, 10×14 cm.

The adhesive dressing may be placed in a bacteria-proof pack, sealed and sterilized by conventional methods including using ethylene oxide or γ-irradiation.

In use the sterile adhesive dressing is removed from the pack, the removable protector is removed, the adhesive layer is applied to the skin of the patient and the support layer may then be removed.

In another aspect therefore the present invention provides a method of treating a wound or indwelling catheter site which comprises applying thereto an adhesive dressing as hereinbefore described by removing the removable protector, applying the adhesive layer to the skin and then removing the support layer.

Preferred embodiments of adhesive dressings of the present invention will now be described by way of example only and with reference to the drawings in which FIG. 1 is a cross-section through one form of a dressing according to the invention within a bacteria-proof package.

Figure 1:
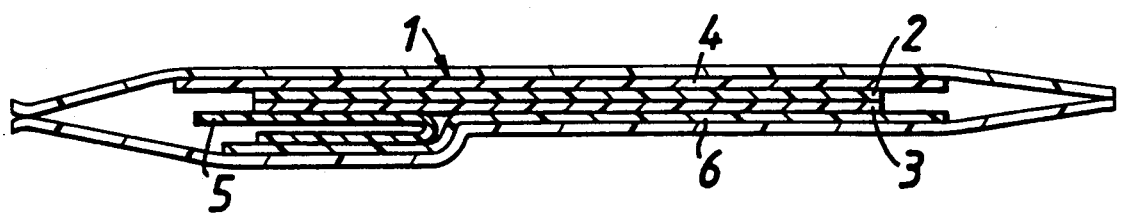

FIG. 1 shows an adhesive dressing (1) which comprises a backing layer (2) formed from a film of a polyether polyurethane. The film has a weight per unit area of 30 gsm and a thickness of 27.5 μm. The backing layer (2) has on one surface a pressure sensitive adhesive layer (3) formed from polyacrylate ester adhesive. The adhesive layer (3) has a weight per unit area of 30 gsm. On the non-adhesive surface of the backing layer (2) is a support layer (4). The support layer (4) may comprise a silicone or polyethylene coated paper or a transparent film of polyethylene or polypropylene. A transparent or translucent support layer (4) may also carry markings for example in the form of a grid whereby the progress of healing wound or ulcer may be measured. The adhesive layer (3) is covered by a removable protectors (5, 6) made from a silicone coated release paper. The removable protectors (5, 6) and support layer (4) extend beyond the backing layer (2). The smaller piece (5) is folded into a V shape. The larger piece (6) is essentially flat and overlaps onto the smaller piece (5).

The length of the adhesive part of a typical small wound or I.V. dressing is 10 cm and its width 12.0 cm. The dressing may be packaged in a sealed peelable pouch and sterilized by ethylene oxide gas.

In use the larger piece (6) is removed first and the dressing held by the overlying portion of piece (5) and edge of the support layer (4). In such a case the larger area of the dressing is adhered to the skin, then the smaller piece (5) and the support layer (4) may be removed. Alternatively, the smaller protector piece (5) may be removed before application and the dressing handled aseptically by the edges of the support layer (4) which project beyond the adhesive (3) and film (2) layers.

Figure 2:
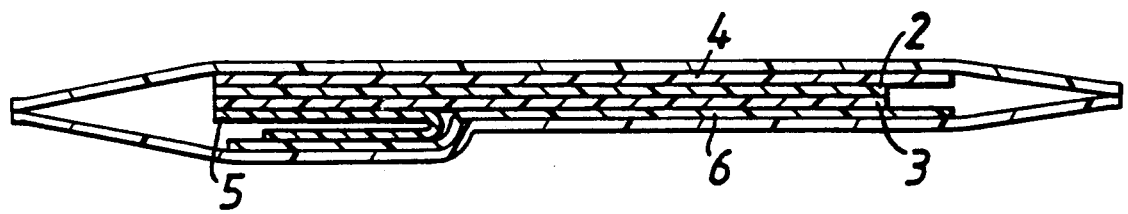
FIG. 2 is a cross-section of a dressing similar to that shown in FIG. 1 but in which only the right-hand edge of the backing and adhesive layers is trimmed.
Figure 3:
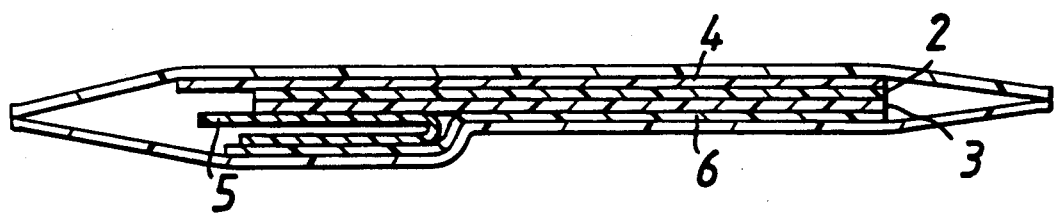
FIG. 3 is a cross-section of a dressing similar to that shown in FIG. 1 but in which the left-hand edge of the backing layer and adhesive layer is trimmed.

FIGS. 2 and 3 show a dressing similar to that shown in FIG. 1 wherein the edges of the dressings have been trimmed on the left-hand and right-hand sides respectively. The support layer (4) and the proctector (6, 7) extend beyond the adhesive and backing layers on the same one edge only.

What is claimed is:

1. A packaged sterile dressing comprising a sterile adhesive dressing within a bacteria-proof package which dressing comprises a backing layer having a pressure sensitive adhesive layer over one surface thereof, a removable protector which covers the adhesive layer and extends beyond the backing layer at one or more edges and a conformable support layer which is reversibly attached to the non-adhesive surface of the backing layer and extends beyond the backing layer at one or more of said edges, wherein said protector comprises first and second parts, the first part having a portion extending away from the adhesive surface and bent back to form a V-shape and the second part having a portion extending away from the adhesive surface and overlying the V-shaped first part.

2. A dressing according to claim 1 wherein the support layer is a transparent sheet material.

3. A dressing according to claim 1, wherein said second protector part covers a major part of the adhesive layer.

4. A dressing according to claim 1, wherein at least one end of the ends of the first part of the protection sheet extends beyond the edge of the backing layer.

5. A dressing according to claim 4 wherein both ends of the first part of the protector extends beyond the edge of the backing layer.

6. A dressing according to claim 1, wherein the overlying portion of the second part of the protector extends beyond the edge of the backing layer.

7. A dressing according to claim 1, wherein the protector extends beyond opposed edges of the backing layer.

8. A dressing according to claim 1, wherein the support layer extends beyond the edge of the backing layer further than the protector extends beyond the edge of the backing layer.

9. A dressing according to claim 1, in which the backing layer is moisture vapour permeable.

10. A dressing according to claim 9 wherein the backing layer has a moisture vapour transmission rate of at least 1200 gm$^{-2}$.

11. A dressing according to claim 1, wherein the backing layer is a film of polyester of polyether polyurethane, an elastomeric polyether polyester or polyether polyamide.

12. A dressing according to claim 1, in which the backing layer is a sheet of a hydrophilic polyurethane.

13. A dressing according to claim 1, wherein the support layer is formed from a polymeric film or coated paper.

14. A dressing according to claim 13 wherein the polymeric film is a polyethylene or polypropylene film.

15. A packaged sterile dressing according to claim 1 wherein the support layer, the backing layer and the adhesive layer are each transparent whereby a wound or catheter site can be viewed through the dressing following the removal of protector.

16. A packaged sterile dressing according to claim 1 which consists essentially of a backing layer having a pressure sensitive adhesive layer over one surface thereof, a removable protector which covers the adhesive layer and a conformable support layer.

17. A packaged sterile dressing according to claim 1 which consists essentially of a transparent backing layer having a transparent pressure sensitive adhesive layer over one surface thereof, a removable protector which covers the transparent adhesive layer and extends beyond the backing layer at one or two edges and a transparent conformable support layer which is reversibly attached to the non-adhesive surface of the backing layer.

18. A packaged sterile dressing according to claim 16 wherein the backing layer is from 20 to 80 μm thick and the adhesive layer is from 20 to 40 μm thick.

19. A packaged sterile dressing according to claim 1 wherein the stripping load of the support layer from the backing layer is greater than that of the protector from the backing layer.

20. A packaged sterile dressing according to claim 1 wherein the protector extends less beyond an edge of the backing layer than the corresponding support layer.

* * * * *